United States Patent [19]
Marcy et al.

[11] Patent Number: 5,783,398
[45] Date of Patent: Jul. 21, 1998

US005783398A

[54] HIGH THROUGHPUT ASSAY USING FUSION PROTEINS

[75] Inventors: Alice Marcy, Westfield; Scott P. Salowe, Dayton; Douglas Wisniewski, Monmouth Junction, all of N.J.

[73] Assignee: Merck & Co., Inc., Rahway, N.J.

[21] Appl. No.: 707,792

[22] Filed: Sep. 4, 1996

Related U.S. Application Data

[60] Provisional application No. 60/003,319 Sep. 15, 1995.

[51] Int. Cl.$^6$ .................... G01N 33/53; G01N 33/544; G01N 33/566; G01N 33/68
[52] U.S. Cl. .................. 435/7.1; 435/7.5; 435/7.72; 435/7.8; 435/69.7; 435/71.2; 435/320.1; 530/324; 530/344; 530/350; 530/415; 536/23.4; 536/24.1
[58] Field of Search .................. 435/7.1, 7.5, 7.72, 435/7.8, 69.7, 71.2, 320.1, 849, 969, 973; 530/324, 344, 350, 415, 812, 816, 827; 536/23.4, 24.1; 930/280

[56] References Cited

U.S. PATENT DOCUMENTS

| | | | |
|---|---|---|---|
| 5,279,957 | 1/1994 | Gross | 435/240.2 |
| 5,352,660 | 10/1994 | Pawson | 514/12 |
| 5,434,064 | 7/1995 | Schlessinger et al. | 435/172.3 |
| 5,464,745 | 11/1995 | Mierendorf et al. | 435/6 |
| 5,498,538 | 3/1996 | Kay et al. | 435/69.1 |
| 5,498,597 | 3/1996 | Burakoff et al. | 514/2 |
| 5,534,424 | 7/1996 | Uhlen et al. | 435/91.2 |
| 5,580,979 | 12/1996 | Bachovchin | 540/509 |

FOREIGN PATENT DOCUMENTS 481673   4/1992   European Pat. Off. .

OTHER PUBLICATIONS

Edalji et al. High-level expression of recombinant human FK-binding protein from a fusion precursor. Journal of Protein Chemistry. vol. 11, No. 3, pp. 213–223, 1992.

Gilmer et al. Peptide inhibitors of src SH3–SH2–phosphoprotein interactions. The Journal of Biological Chemistry. vol. 269, No. 50, pp. 31711–31719, Dec. 16, 1994.

Jin et al. The 25–kDa FK506–binding protein is localized in the nucleus and associates with casein Kinase II and nucleolin. Proceedings of the National Academy of Sciences, USA. vol. 90, pp. 7769–7773, Aug. 1993.

Müller et al. Rapid identification of phosphopeptide ligands for SH2 domains: screening of peptide libraries by fluorescence–activated bead sorting. The Journal of Biological Chemistry. vol. 271, No. 28, pp. 16500–16505, Jul. 12, 1996.

Sampson et al. *Neisseria meningitidis* encodes an FK506–inhibitable rotamase. Proceedings of the National Academy of Sciences, USA. vol. 89, pp. 1164–1168, Feb. 1992.

Studier et al. Use of T7 RNA polymerase to direct expression of cloned genes. In: Methods in Enzymology, Academic Press, SanDiego, CA. vol. 185, pp. 60–89, 1990.

Lemmon, et al., "Thermodynamic Studies of Tyrosyl–Phosphopeptide Binding to the SH2 Domain of p56lck", Biochemistry, vol. 33, pp. 5070–5076, 1994.

Payne, et al., "Kinetics of p56lck and p60src Src Homology 2 Domain Binding to Tyrosine–Phosphorylated Peptides Determined by a Competition Assay or Surface Plasmon Resonance", Proc. Natl. Acad. Sci. USA, vol. 90, pp. 4902–4906, 1993.

(List continued on next page.)

*Primary Examiner*—Stephen Walsh
*Assistant Examiner*—Brian Lathrop
*Attorney, Agent, or Firm*—Valerie J. Camara; Mark R. Daniel; Dianne Pecoraro

[57] ABSTRACT

This application describes a high throughput assay for screening for compounds capable of binding to a fusion protein which consists of a target protein and an FK506-binding protein. The method for preparing the DNA encoding for the fusion protein and for expressing that DNA is also described in the application. The invention also discloses the recombinant DNA and protein sequences for several fusion proteins.

42 Claims, 1 Drawing Sheet

OTHER PUBLICATIONS

Isakov, et al., ZAP-70 Binding Specificity to T Cell Receptor Tyrosine-Based Activation Motifs: The Tandem SH2 Domains of ZAP-70 Blind Distinct Tyrosine-Based Activation Motifs with Varying Affinity, J. Exp. Med., vol. 181, pp. 375–380, 1995.

Huyer, et al., "Direct Determination of the Sequence Recognition Requirements of the SH2 Domains of SH–PTP2", Biochemistry, vol. 34, pp. 1040–1049, 1995.

Panayotou, et al., "Interactions Between SH2 Domains and Tyrosine–Phosphorylated Platelet–Derived Growth Factor Beta–Receptor Sequences: Analysis of Kinetic Parameters by a Novel Biosensor–Based Approach", Mol. Cell. Biol., vol. 13, pp. 3567–3576, 1993.

Felder, et al., "SH2 Domains Exhibit High–Affinity Binding to Tyrosine–Phosphorylated Peptides Yet Also Exhibit Rapid Dissociation and Exchange", Mol. Cell. Biol., vol. 13, pp. 1449–1455, 1993.

Morelock, et al., "Determination of Receptor–Ligand Kinetic and Equilibrium Binding Constants Using Surface Plasmon Resonance: Application to the lck SH2 Domain and Phosphotyrosyl Peptides", J. Med. Chem., vol. 38, pp. 1309–1318, 1995.

Ladbury, et al., "Measurement of the Binding of Tyrosyl Phosphopeptides to SH2 Domains: A Reappraisal", Proc. Natl. Acad. Sci. USA, vol. 92, pp. 3199–3203, 1995.

Piccione, et al., "Phosphatidylinositol 3–Kinase p85 SH2 Domain Specificity of Defined by Direct Phosphopeptide/SH2 Domain Binding", Biochemistry, vol. 32(13), pp. 3197–3202, 1993.

Sonatore, et al., "The Utility of FK506–Binding Protein as a Fusion Partner in Scintillation Proximity Assays: Application to SH2 Domains", Anal. Biochemistry, vol. 240, pp. 289–297, 1996.

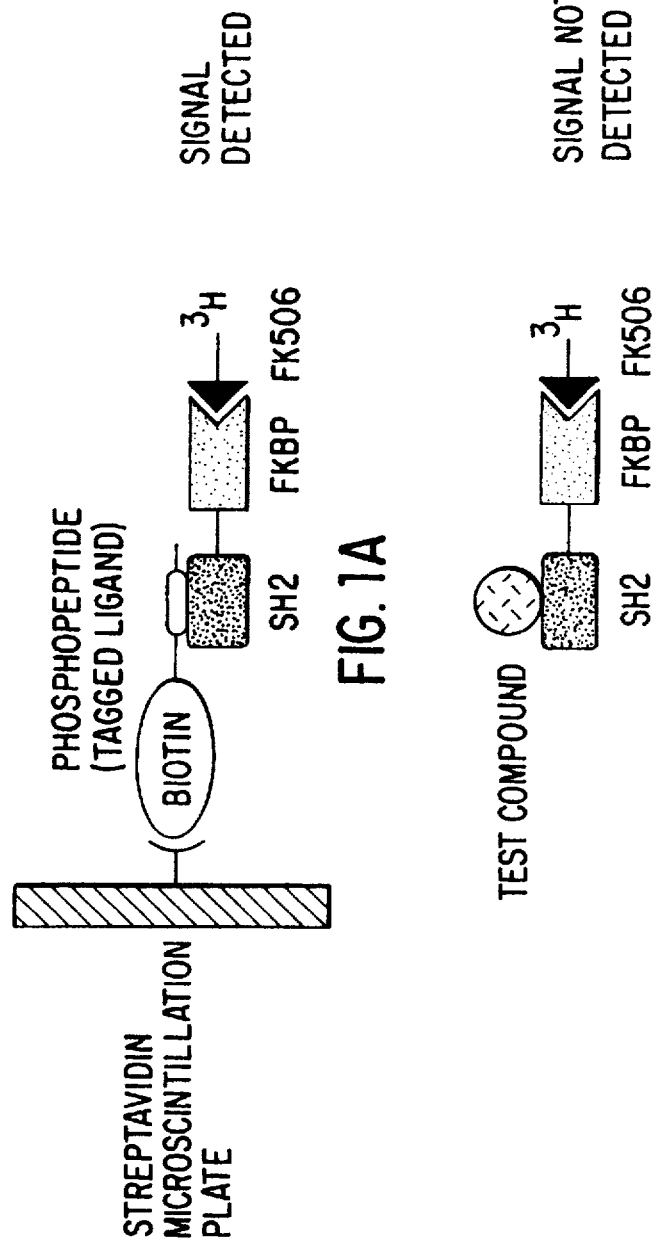

HIGH THROUGHPUT ASSAY USING FUSION PROTEINS

DOMESTIC PRIORITY CLAIM

The priority of U.S. Provisional Application No. 60/003,319, filed on Sep. 15, 1995, now abandoned, is claimed.

BACKGROUND OF THE INVENTION

Src homology 2 (SH2) domains are a family of homologous protein domains that share the common property of recognizing phosphorylated tyrosine residues in specific peptide contexts. They have routinely been expressed in *E. coli* as fusion proteins with glutathione-S-transferase (GST). This usually provides high level expression and straightforward affinity purification on glutathione-Sepharose. Ligand binding is then assayed by incubating the GST/SH2 with a radiolabeled phosphopeptide, precipitating the complex with glutathione-Sepharose, washing the beads, and then counting the beads to determine bound radioactivity [Isakov et al., *J. Exp. Med.*, 181, 375–380 (1995); Piccione et al., *Biochemistry*, 32, 3197–3202 (1993); Huyer et al., *Biochemistry*, 34, 1040–1049 (1995)]. There are several disadvantages to this procedure, particularly when applied to high-throughput screening for agonists, antagonists, or inhibitors as new leads for drug development. First, the radiolabeling of the peptide is carried out either enzymatically with a kinase and [$^{32}$P]ATP or chemically with [$^{125}$I] Bolton-Hunter reagent. In both cases, the isotopes are short-lived and thus require frequent preparation of material. In the case of enzymatic phosphorylation, the appropriate kinase must also be available in sufficient quantity to generate enough material for screening purposes. Second, the protocol requires separation of bound complex from free phosphopeptide by washing of the glutathione-Sepharose beads. This is a nonequilibrium procedure that risks dissociation of the bound ligand, particularly when off-rates are fast. Thus, there is the possibility of misleading results. Finally, due to the number of manipulations and centrifugations involved, the protocol is very tedious to conduct manually and is not readily adaptable to robotic automation to increase throughput.

Two additional methods for measuring the interaction of proteins and ligands that have been applied to SH2 domains are biospecific interaction analysis using surface plasmon resonance and isothermal titration calorimetry (Felder et al., *Mol. Cell. Biol.*, 13, 1449–1455 (1993); Panayotou et al., *Mol. Cell. Biol.*, 13, 3567–3576 (1993); Payne et al., *Proc. Natl. Acad. Sci. U.S.A.*, 90, 4902–4906 (1993); Morelock et al., *J. Med. Chem.* 38, 1309–18 (1995); Ladbury et al., *Proc. Natl. Acad. Sci. U.S.A.*, 92, 3199–3203 (1995); Lemmon et al., *Biochemistry*, 33, 5070–5076 (1994)). These techniques do not require a particular fusion partner for the SH2 domain, but do require sophisticated instrumentation that is not amenable to high throughput screening.

SUMMARY OF THE INVENTION

The instant invention covers a method of screening for compounds capable of binding to a fusion protein which comprises combining a test compound, a tagged ligand, a fusion protein (target protein, peptide linker and FK506-binding protein), and a radiolabeled ligand in a coated microscintillation plate, and then measuring the scintillation counts attributable to the binding of the tagged ligand to the fusion protein in the presence of the test compound relative to a control assay in the absence of the test compound, so as to determine the effect the test compound has on the binding of the tagged ligand. Also within the scope of this invention are the processes for preparing and expressing the recombinant DNA encoding a fusion protein. This invention further relates to the recombinant DNA expression vector capable of expressing the fusion protein. This invention further relates to a process for purifying the recombinant fusion protein. This invention provides an immediate means of making use of microscintillation plate technology for the functional assay of ligand binding to a single or multiple signal transduction domain(s), for example a phosphopeptide binding to an SH2 domain. The present invention does not require specialized radiochemical synthesis and is readily adaptable to robotic automation for high capacity screening for agonists, antagonists, and/or inhibitors.

BRIEF DESCRIPTION OF THE FIGURES

FIG. 1.

A.) Binding of the streptavidin microscintillation plate, biotinylated ligand and the fusion protein (SH2:FKBP), which emits a detectable signal; and B.) Binding of the test compound and the fusion protein (SH2:FKBP), which results in no signal detection.

DETAILED DESCRIPTION OF THE INVENTION

The present invention relates to a method of screening for compounds which preferentially bind to a target protein.

An embodiment of this invention is a method of screening for compounds capable of binding to a fusion protein which comprises the steps of:

a) mixing a test compound, a tagged ligand, the fusion protein, and a radiolabeled ligand;

b) adding the mixture to a coated microscintillation plate;

c) incubating the mixture for between about 1 hour and about 24 hours;

d) measuring the plate-bound counts attributable to the binding of the tagged ligand to the fusion protein in the presence of the test compound using scintillation counting; and e) determining the binding of the tagged ligand to the fusion protein in the presence of the test compound relative to a control assay run in the absence of the test compound.

A second embodiment of this invention is a process for preparing a recombinant DNA expression vector encoding for a fusion protein comprising the steps of:

a) removing the stop codon on DNA encoding for an FK506-binding protein;

b) synthesizing a modified DNA fragment on the DNA encoding for the FK506-binding protein which encodes for a peptide linker;

c) digesting an expression vector at cloning sites;

d) cloning the modified DNA fragment encoding for the FK506-binding protein with a peptide linker into the digested expression vector to generate a recombinant DNA expression vector encoding for FK506-binding protein with a peptide linker; and e) cloning DNA encoding for a target protein into a recombinant DNA expression vector encoding for FK506-binding protein with a peptide linker to produce the recombinant DNA expression vector encoding for the fusion protein.

A third embodiment of this invention is a process for expressing recombinant DNA encoding for a fusion protein in an expression vector comprising the steps of:

a) transforming a host cell with the fusion protein expression vector;

b) inducing expression of the fusion protein in the host cell;

c) recovering the fusion protein from the host cell; and d) purifying the fusion protein.

A fourth embodiment of this invention is a process for purifying an isolated FKBP-SH2 fusion protein, comprising the steps of:

a) preparing an affinity matrix consisting of biotinylated phosphopeptide coupled to avidin or streptavidin immobilized on a solid support;

b) preparing a freeze/thaw extract from cells expressing the fusion protein;

c) loading the extract onto the affinity matrix and washing off unbound protein; and d) eluting the desired fusion protein with phenyl phosphate.

The term "fusion protein" refers to a "target protein" fused to an "FK506-binding protein" (FKBP), the two proteins being separated by a "peptide linker".

A "peptide linker" may consist of a sequence containing from about 1 to about 20 amino acids, which may or may not include the sequence for a protease cleavage site. An example of a peptide linker which is a protease cleavage site is represented by the amino acid sequence GLVPRGS (SEQ.ID.NO.7).

The term "target protein" refers to any protein that has a defined ligand. Included within this definition of target protein are single and multiple signal transduction domains, such as, but not limited to, Src homology 1 (SH1), Src homology 2 (SH2), Src homology 3 (SH3), and pleckstrin homology (PH) domains [Hanks & Hunter, FASEB J., 9, 576–596 (1995); Bolen, Curr. Opin. Immunol., 7, 306–311 (1995); Kuriyan & Cowburn, Curr. Opin. Struct. Biol., 3, 828–837 (1993); Cohen et al., Cell, 80, 237–248 (1995)]. The term "SH1 domain" refers to a family of homologous protein domains that bind ATP and catalyze tyrosine phosphorylation of peptide and protein substrates. The term "SH2 domain" refers to a family of homologous protein domains that share the common property of recognizing phosphorylated tyrosine residues in specific peptide contexts. The term "SH3 domain" refers to a family of homologous protein domains that share the common property of recognizing polyproline type II helices. The term "PH domain" refers to a family of homologous protein domains that mediate both protein-protein and protein-lipid interactions. Examples of SH2 domains which may be utilized in the method of the invention include, but are not limited to, the single and tandem SH2 domains present in the tyrosine kinases ZAP, SYK and LCK. The DNA sequences were obtained from GenBank, National Center for Biotechnology Information, National Library of Medicine, 8600 Rockville Pike, Bethesda, Md. 20894. The Accession Numbers for the sequences are: human ZAP (L05148); human SYK (L28824) and human LCK (X13529).

The sequences for ZAP, Syk and Lck are disclosed in the sequence lising as follows: the isolated DNA encoding for a fusion protein containing ZAP is (SEQ.ID.NO. 1); the isolated DNA encoding for a fusion protein containing Syk is (SEQ.ID.NO. 2); the isolated DNA encoding for a fusion protein containing Lck is (SEQ.ID.NO. 3); the sequence for the FKBP-ZAP:SH2 fusion protein is (SEQ.ID.NO. 4); the sequence for the FKBP-Syk:SH2 fusion protein is (SEQ.ID.NO. 5); and the sequence for the FKBP-Lck:SH2 fusion protein is (SEQ.ID.NO. 6).

The term "tagged ligand" refers to a biotinylated or epitope tagged ligand for the target protein.

The term "radiolabeled ligand" refers to a $[^3H]$-, $[125I]$-, $[^{14}C]$-, $[^{35}S]$-, $[^{32}P]$-, or $[^{33}P]$-labeled ligand which binds to the FKBP.

An example of a radiolabeled ligand useful in the instant invention is $[^3H]$-dihydroFK506.

The term "coated microscintillation plates" refers to streptavidin-coated microscintillation plates when the tagged ligand is biotinylated, and to anti-epitope antibody bound to anti-antibody-coated or protein A-coated microscintillation plates when the tagged ligand is epitope-tagged. Examples of coated microscintillation plates useful in the instant invention are streptavidin-coated, sheep anti-rabbit-coated, and goat anti-mouse-coated FlashPlate Plus (DuPont-NEN). Additional coatings, including but not limited to protein A, may be applied to uncoated FlashPlates by methods known to those skilled in the art.

The term "control assay" refers to the assay when performed in the presence of the tagged ligand, the fusion protein, the radiolabeled ligand and the coated microscintillation plates, but in the absence of the test compound.

The term FK506-binding proteins may include, but are not limited to, the below listed FKBPs and FKBP homologues, which include a citation to the references which disclose them. This list is not intended to limit the scope of the invention.

| Mammalian | |
| --- | --- |
| FKBP-12 | Galat et al., Eur. J. Biochem., 216:689–707 (1993). |
| FKBP-12.6 | Wiederrecht, G. and F. Etzkorn Perspectives in Drug Discovery and Design, 2:57–84 (1994). |
| FKBP-13 | Galat et al., supra; Wiederrecht and Etzkorn, supra. |
| FKBP-25 | Galat et al., supra; Wiederrecht and Etzkorn, supra. |
| FKBP-38 | Wiederrecht and Etzkorn, supra. |
| FKBP-51 | Baughman et al., Mol. Cell. Biol., 8, 4395–4402(1995). |
| FKBP-52 | Galat et al., supra. |
| Bacteria | |
| Legionella pneumophilia | Galat et al., supra. |
| Legionella micadei | Galat et al., supra. |
| Chlamydia trachomatis | Galat et al., supra. |
| E. coli fkpa | Horne, S. M. and K. D. Young, Arch. Microbiol., 163:357–365 (1995). |
| E. coli slyD | Roof et al., J. Biol. Chem, 269:2902–2910 (1994). |
| E. coli orf149 | Trandinh et al., FASEB J. 6:3410–3420 (1992). |
| Neisseria meningitidis | Hacker, J. and G. Fischer, Mol. Micro., 10:445–456 (1993). |
| Streptomyces chrysomallus | Hacker and Fischer, supra. |
| Fungal | |
| yeast FKBP-12 | Cardenas et al., Perspectives in Drug Discovery and Design, 2:103–126 (1994). |
| yeast FKBP-13 | Cardenas et al., supra. |
| yeast NPR1(FPR3) | Cardenas et al., supra. |
| Neurospora | Galat et al., supra. |

A variety of host cells may be used in this invention, which include, but are not limited to, bacteria, yeast, blue-green algae, plant cells, insect cells and animal cells.

Expression vectors are defined herein as DNA sequences that are required for the transcription of cloned copies of genes and the translation of their mRNAs in an appropriate host. Such vectors can be used to express genes in a variety of host cells, such as, bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available vectors suitable for FKBP fusion protein expression include, but are not limited to pBR322 (Promega), pGEX (Amersham), pT7 (USB), pET (Novagen), pIBI (IBI), pProEX-1 (Gibco/BRL), pbluescript II (Stratagene), pTZ18R and pTZ19R (USB), pSE420 (Invitrogen), pVL1392 (Invitrogen), pBlueBac (Invitrogen), pBAcPAK (Clontech), pHIL (Invitrogen), pYES2 (Invitrogen), pCDNA (Invitrogen), pREP (Invitrogen) or the like.

The expression vector may be introduced into host cells via any one of a number of techinques including but not limited to transformation, transfection, infection, protoplast fusion, and electroporation.

*E. coli* containing an expression plasmid with the target gene fused to FKBP are grown and appropriately induced. The cells are then pelleted and resuspended in a suitable buffer. Although FKBP-12 lacks sequences that specifically direct it to the periplasm, FKBP fusions are primarily located there and can be released by a standard freeze/thaw treatment of the cell pellet. Following centrifugation, the resulting supernatant contains >80% pure FKBP fusion, which if desired can be purified further by conventional methods. Alternatively, the assay is not dependent on pure protein and the initial periplasmic preparation may be used directly. A thrombin site located between FKBP and the target protein can be used as a means to cleave FKBP from the fusion; such cleaved material may be a suitable negative control for subsequent assays.

A fusion protein which contains a single or multiple SH2 domain(s) may be purified by preparing an affinity matrix consisting of biotinylated phosphopeptide coupled to avidin or streptavidin immobilized on a solid support. A freeze/ thaw extract is prepared from the cells which express the fusion protein and is loaded onto the affinity matrix. The desired fusion protein is then specifically eluted with phenyl phosphate.

To assay the formation of a complex between a target protein and its ligand, the tagged ligand is mixed with the FKBP fusion protein in a suitable buffer in the presence of the radiolabeled ligand. After a suitable incubation period to allow complex formation to occur, the mixture is transferred to a coated microscintillation plate to capture the tagged ligand and any bound fusion protein. The plate is sealed, incubated for a sufficient period to allow the capture to go to completion, then counted in a multiwell scintillation counter. Screening for agonists/antagonists/inhibitors is carried out by performing the initial incubation prior to the capture step in the microscintillation plate in the presence of a test compound(s) to determine whether they have an effect upon the binding of the tagged ligand to the fusion protein. This principle is illustrated in FIG. 1.

The present invention can be understood further by the following examples, which do not constitute a limitation of the invention.

EXAMPLE 1

Process for Preparing the FKBP fusion cloning vector

General techniques for modifying and expressing genes in various host cells can be found in Ausubel, F. M., Brent, R., Kingston, R. E., Moore, D. D., Seidman, J. G., Smith, J. A. and Struhl, K. Current Protocols in Molecular Biology (John Wiley & Sons, New York, N.Y., 1989). Sequences for a 3'-altered FKBP fragment that contained a glycine codon (GGT) in place of the stop (TGA) codon followed by a sequence encoding a thrombin site (Leu-Val-Pro-Arg) and BamHI restriction site (GAATTC) were amplified using the polymerase chain reaction (PCR). The PCR reaction contained the following primers:5'-GATCGCCATGGG AGTGCAGGTGGAAACCATCTCCCA-3' (SEQ.ID.NO.8) and 5'-TACGAATTCTGGCGTGGATCCA CGCGGAACCAGACCTTCCAGT TTTAG-3' (SEQ.ID.NO.9) and a plasmid containing human FKBP-12 as the template. The resulting 367 base pair amplification product was ligated into the vector pCRII (Invitrogen) and the ligation mixture transformed into competent *Escherichia coli* cells. Clones containing an insert were identified using PCR with flanking vector primers. Dideoxy DNA sequencing confirmed the nucleotide sequence of one positive isolate. The altered 338 base pair FKBP fragment was excised from the pCRII plasmid using NcoI and BamHI and ligated into NcoI and BamHI digested pET9d (Novagen) plasmid. Competent *E. coli* were transformed with the ligation mixture, and colonies containing the insert were identified using PCR with primers encoding for flanking vector sequences. The FKBP fusion cloning vector is called pET9dFKBPt.

EXAMPLE 2

Process for Preparing the FK-ZAP fusion expression vector

A DNA fragment encoding for the tandem SH2 domains of ZAP-70 was prepared by PCR to contain a BamHI site at the 5'-end such that the reading frame was conserved with that of FKBP in the fusion vector. At the 3'-end, the fragment also incorporated a stop codon followed by a BamHI site. The PCR reaction contained Molt-4 cDNA (Clontech) and the following primers: 5'-ATTAGGATCCATGCCA GATCCTGCAGCTCACCTGCCCT-3' (SEQ.ID.NO.10) and 5'-ATATGGATCCTTACCAGAGGCGTTGCT-3' (SEQ.ID.NO.11). The fragment was cloned into a suitable vector, sequenced, digested with BamHI, and the insert containing the SH2 domains ligated to BamHI treated pET9dFKBPt, and transformed into *E. coli*. Clones containing inserts in the correct orientation were identified by PCR or restriction enzyme analysis. Plasmid DNA was prepared and used to transform BL21(DE3) cells.

EXAMPLE 3

Process for Preparing the FK-SYK fusion expression vector

The expression vector for the tandem SH2 domains of Syk fused to FKBP was prepared as in Example 2 except that the PCR reaction contained Raji cell cDNA (Clontech) and the following primers: 5'-CAATAGGATCCAT GGCCAGCAGCGGCATGGCTGA-3' (SEQ.ID.NO.12) and 5'-GACCTAGGATCCCTAATTAACATTTCCCT GTGTGCCGAT-3' (SEQ.ID.NO.13)

EXAMPLE 4

Process for Preparing the FK-LCK fusion expression vector

The expression vector for the SH2 domain of Lck fused to FKBP was prepared as in Example 2 except that the PCR reaction contained Molt-4 cDNA (Clontech) and the following primers:

5'-ATATGGATCCATGGCGAACAGCCTGGAGCCC GAACCCT-3' (SEQ.ID.NO.14)

and

5'-ATTAGGATCCTTAGGTCTGGCAGGGGCGGCT CAACCGTG TGCA-3' (SEQ.ID.NO.15).

EXAMPLE 5

FK-ZAP

Step A: Process for Expression of FK-ZAP

E. coli BL21 (DE3) cells containing the pET9dFKBPt/ZapSH2 plasmid were grown in Luria-Bertani (LB) media containing 50 microgram/ml kanamycin at about 37 degrees C. until the optical density measured at 600 nm was about 0.5–1.0. Expression of the FK-ZAP fusion protein was induced with 0.1 mM isopropyl beta-thiogalactopyranoside and the cells were grown for another 3–5 hr at about 30 degrees C. They were pelleted at 4400 x g for about 10 min at about 4 degrees C. and resuspended in 2% of the original culture volume with 100 mM tris pH 8.0 containing 1 microgram/ml each aprotinin, pepstatin, leupeptin, and bestatin. The resuspended pellet was frozen at about −20 degrees C. until further purification.

Step B: Process for Purification of FK-ZAP

The affinity matrix for purification of FK-ZAP was prepared by combining agarose-immobilized avidin with excess biotinylated phosphopeptide derived from the ζ1 ITAM sequence of the human T-cell receptor, biotinyl-GSNQLpYNELNLGRREEpYDVLDK (SEQ.ID.NO.16), and washing out unbound peptide. Frozen cells containing FK-ZAP were thawed in warm water, refrozen on dry ice for about 25 min., then thawed again. After the addition of 0.1 % octyl glucoside, 1 mM dithiothreitol (DTT) and 500 mM NaCl, the extract was centrifuged at 35,000 x g for approximately 30 minutes. The supernatant was loaded onto the phosphopeptide affinity column, at about 4° and washed with phosphate buffered saline containing 1 mM DTT and 0.1 % octyl glucoside. FK-ZAP was eluted with 200 mM phenyl phosphate in the same buffer at about 37°. The protein pool was concentrated and the phenyl phosphate removed on a desalting column. The purified FK-ZAP was stored at about −30° in 10 mM HEPES/150 mM NaCl/1 mM DTT/0.1 mM EDTA/10% glycerol.

EXAMPLE 6

FK-SYK

E. coli BL21 (DE3) cells containing the pET9dFKBPt/SykSH2 plasmid were grown, induced, and harvested as described in Example 5. FK-SYK was purified using the same affinity matrix and methodology described in Example 5.

EXAMPLE 7

FK-LCK

E. coli BL21 (DE3) cells containing the pET9dFKBPt/LckSH2 plasmid were grown, induced, and harvested as described in Example 5. The affinity matrix for purification of FK-LCK was prepared by combining agarose-immobilized avidin with excess biotinyl- EPQpYEEIPIYL (SEQ.ID.NO.17), and washing out unbound peptide. The remaining methodology for purification was the same as Example 5.

EXAMPLE 8

Assay of phosphopeptide binding to FK-ZAP

Assays were conducted at ambient temperature in a buffer consisting of 25 mM HEPES, 10 mM DTT, 0.01% TWEEN-20, pH 7.0. 300 µl of a mixture of buffer and varying amounts of biotinyl-phosphopeptide were combined with 25 µl of FK-ZAP protein and 50 µl of [$^3$H]-dihydroFK506 (DuPont NEN) in microfuge tubes. A 150 µl portion of each assay was then transferred to the well of a streptavidin-coated FlashPlate Plus (DuPont-NEN) and an additional 50 µl of buffer was added. Final concentrations of the assay components were:

0–50 nM biotinyl-GSNQLpYNELNLGRREEpYDVLDK (SEQ.ID.NO.16)

100 nM FK-ZAP fusion protein 25 nM [$^3$H]-dihydroFK506

The plate was sealed and incubated 20 hours. Plate-bound radioactivity was measured at various timepoints in a Packard Topcount microplate scintillation counter.

EXAMPLE 9

Method of Screening for Antagonists of FK-ZAP

Assays are conducted at ambient temperature in a buffer consisting of 25 mM HEPES, 10 mM DTT, 0.01% TWEEN-20, pH 7.0. 10 µl of a DMSO solution of test compound(s) and 120 µl of biotinyl-phosphopeptide stock solution are dispensed into the wells of a standard 96-well plate. Next, 20 µl of a mixture of FK-ZAP protein and [$^3$H]-dihydroFK506 (DuPont NEN) are added to each test well. The assays are then transferred to the wells of a streptavidin-coated Flash-Plate (DuPont NEN). Final concentrations of the assay components are:

25nM biotinyl-GSNQLpYNELNLGRREEpYDVLDK (SEQ.ID.NO.16)

25 nM FK-ZAP fusion protein 10 nM [$^3$H]-dihydroFK506

5% DMSO

The plate is sealed and incubated between 1 and 8 hours. Bead-bound radioactivity is then measured in a Packard Topcount microplate scintillation counter.

EXAMPLE 10

Method of Screening for Antagonists of FK-SYK

The assays are conducted as set forth in Example 9, except that FK-SYK replaces FK-ZAP.

EXAMPLE 11

Method of Screening for Antagonists of FK-LCK

The assays are conducted as set forth in Example 9, except that FK-LCK replaces FK-ZAP and the tagged ligand is 25 nM biotinyl-EPQpYEEIPIYL (SEQ.ID.NO.17).

What is claimed is:

1. A method of screening for compounds capable of binding to a fusion protein, which is defined as an FK506-binding protein linked to a target protein through a peptide linker, which -comprises the steps of:

a) mixing a test compound, a tagged- ligand for the target protein, which is selected from a biotinylated ligand or an epitope-tagged ligand, the fusion protein, a radiolabeled ligand selected from [$^3$H]- or [$^{125}$I]-labeled F506 analog and a coated microscintillation plate selected from a streptavidin-coated or anti-antibody coated or protein A-coated microscintillation plates;

b) incubating the mixture from between about 1 hour to about 24 hours;

c) measuring the plate-bound counts attributable to the binding of the tagged ligand to, the fusion protein in the presence of the test compound using scintillation counting; and d) determining the binding of the tagged ligand to the fusion protein in the presence of the test compound relative to a control assay run in the absence of the test compound.

2. The method of screening for compounds capable of binding to a fusion protein, as recited in claim 1, wherein the target protein comprises a single or multiple signal transduction domain.

3. The method for screening for compounds capable of binding to a fusion protein, as recited in claim 2, wherein the single or multiple signal transduction domain is selected from the group consisting of: SH1, SH2, SH3 and PH domains.

4. The method of screening for compounds capable of binding to a fusion protein, as recited in claim 3, wherein the target protein is a single or multiple SH2 domain.

5. The method of screening for compounds capable of binding to a fusion protein, as recited in claim 4, wherein the radiolabeled ligand is [$^3$H]-dihydroFK506.

6. The method of screening for compounds capable of binding to a fusion protein, as recited in claim 5, wherein the FK506-binding protein is a 12 kDA human FK506-binding protein.

7. The method of screening for compounds capable of binding to a fusion protein, as recited in claim 6, wherein the target protein is a single or multiple SH2 domain selected from the group consisting of: ZAP:SH2, SYK:SH2 and LCK:SH2.

8. The method of screening for compounds capable of binding to a fusion protein, as recited in claim 7, wherein the target protein is the SH2 domain, ZAP:SH2.

9. The method of screening for compounds capable of binding to a fusion protein, as recited in claim 7, wherein the target protein is the SH2 domain, SYK:SH2.

10. The method of screening for compounds capable of binding to a fusion protein, as recited in claim 7, wherein the target protein is the SH2 domain, LCK:SH2.

11. A process for preparing a recombinant DNA expression vector encoding for a fusion protein, which is defied as an FK506-binding protein linked to a target protein through a peptide linker, comprising the steps of:

a) removing the stop codon on DNA encoding for the FK506-binding protein;

b) synthesizing a modified DNA fragment on the DNA encoding for the FK506-binding protein which encodes for a peptide linker;

c) digesting an expression vector at cloning sites;

d) cloning the modified DNA fragment encoding for the FK506-binding protein with a peptide linker into the digested expression vector to generate a recombinant DNA expression vector encoding for FK506-binding protein with a peptide linker; and e) cloning DNA -encoding for a target protein into a recombinant DNA expression vector encoding for FK506-binding protein with a peptide linker to produce the recombinant DNA expression vector encoding for the fusion protein.

12. The process for preparing a recombinant DNA expression vector encoding the fusion protein, as recited in claim 11, wherein the target protein is a single or multiple signal transduction domain.

13. The process for preparing a recombinant DNA expression vector encoding the fusion protein, as recited in claim 12, wherein the single or multiple signal transduction domain is selected from the group consisting of: SH1, SH2, SH3 and PH domains.

14. The process for preparing a recombinant DNA expression vector encoding the fusion protein, as recited in claim 13, wherein the single or multiple signal transduction domain is an SH2 domain.

15. The process for preparing a recombinant DNA expression vector encoding the fusion protein, as recited in claim 14, wherein the single or multiple signal transduction domain is an SH2 domain selected from the group consisting of ZAP:SH2, SYK:SH2 and LCK:SH2.

16. The process for preparing a recombinant DNA expression vector encoding the fusion protein, as recited in claim 15, wherein the FK506-binding protein is a 12 kDa FK506 binding protein.

17. The process for preparing a recombinant DNA expression vector encoding the fusion protein, as recited in claim 16, wherein the target protein is ZAP:SH2.

18. The process for preparing a recombinant DNA expression vector encoding the fusion protein, as recited in claim 16, wherein the target protein is SYK:SH2.

19. The process for preparing a recombinant DNA expression vector encoding the fusion protein, as recited in claim 16, wherein the target protein is LCK:SH2.

20. Isolated DNA encoding for a fusion protein comprising the sequence:

(SEQ. ID. NO. 1).

21. Isolated DNA encoding for a fusion protein comprising the sequence:

(SEQ. ID. NO. 2).

22. Isolated DNA encoding for a fusion protein comprising the sequence:

(SEQ. ID. NO. 3).

23. A FKBP-ZAP:SH2 fusion protein comprising the sequence:

(SEQ. ID. NO. 4).

24. A FKBP-SYK:SH2 fusion protein comprising the sequence:

(SEQ. ID. NO. 5).

25. A FKBP-LCK:SH2 fusion protein comprising the sequence:

(SEQ. ID. NO. 6).

26. A process for expressing recombinant DNA encoding for a fusion protein, which is defined as a-FK506-binding protein linked to a target protein through a peptide linker in an expression vector comprising the steps of;

a) transforming a host cell with the fusion protein expression vector;

b) inducing expression of the fusion protein in the host cell;

c) recovering the fusion protein from the host cell; and d) purifying the fusion protein.

27. The process for expressing recombinant DNA encoding a fusion protein, as recited in claim 26, wherein the target protein is a single or multiple signal transduction domain.

28. The process for expressing recombinant DNA encoding a fusion protein, as recited in claim 27, wherein the single or multiple signal transduction domain is selected from the group consisting of: SH1, SH2, SH3 and PH domains.

29. The process for expressing recombinant DNA encoding a fusion protein, as recited in claim 28, wherein the single or multiple signal transduction domain is a single or multiple SH2 domain.

30. The process for expressing recombinant DNA encoding a fusion protein, as recited in claim 29, wherein the single or multiple SH2 domain is selected from a group consisting of ZAP:SH2, SYK:SH2 and LCK:SH2.

31. The process for expressing recombinant DNA encoding a fusion protein, as recited in claim 30, wherein the FK506-binding protein is human 12kDa FK506-binding protein.

32. The process for expressing recombinant DNA encoding a fusion protein, as recited in claim 31, wherein the host cell is from bacteria, yeast, blue green algae, plant cells, insect cells, or animal cells.

33. The process for expressing recombinant DNA encoding a fusion protein, as recited in claim 32, wherein the host cell is an *E. coli* strain selected from a group consisting of BL21 (DE3), Nova Blue (DE3), and JM109 (DE3).

34. The process for expressing recombinant DNA encoding a fusion protein, as recited in claim 33, wherein the single or multiple SH2 domain is ZAP:SH2.

35. The process for expressing recombinant DNA encoding a fusion protein, as recited in claim 33, wherein the single or multiple SH2 domain is SYK:SH2.

36. The process for expressing recombinant DNA encoding a fusion protein, as recited in claim 33, wherein the single or multiple SH2 domain is LCK:SH2.

37. The process for purifying an isolated FKBP-SH2 fusion protein comprising the steps of:
   a) preparing an affinity matrix consisting of biotinylated phosphopeptide coupled to avidin or streptavidin immobilized on a solid support;
   b) preparing a freeze/thaw extract from cells expressing the fusion protein;
   c) loading the extract onto the affinity matrix and washing off unbound protein; and
   d) eluting the desired fusion protein with phenyl phosphate.

38. A recombinant FKBP-SH2 domain T7 RNA polymerase-based expression vector, wherein the DNA encodes for the FKBP-ZAP:SH2 fusion protein and has the DNA sequence (SEQ. ID. NO.1).

39. A recombinant FKBP-SH2 domain T7 RNA polymerase-based expression vector, wherein the DNA encodes for the FKBP-SYK:SH2 fusion protein and has the DNA sequence (SEQ. ID. NO. 2).

40. A recombinant FKBP-SH2 domain T7 RNA polymerase-based expression vector, wherein the DNA encodes for the FKBP-LCK:SH2 fusion protein and has the DNA sequence (SEQ. ID. NO.3).

41. A recombinant host cell containing the recombinant FKBP-SH2 domain T7 RNA polymerase-based expression vector wherein the recombinant host cell is selected from the group consisting of: *E. coli* BL21 (DE3), *E. coli* Nova Blue (DE3), and *E. coli* JM109 (DE3).

42. The recombinant host cell containing the recombinant FKBP-SH2 domain T7 RNA polymerase-based expression vector as recited in claim 41, wherein the recombinant host cell is *E. coli* BL21 (DE3).

* * * * *

UNITED STATES PATENT AND TRADEMARK OFFICE
CERTIFICATE OF CORRECTION

PATENT NO. : 5,783,398     (Case Docket No. 19524)

DATED : 7/21/98

INVENTOR(S) : Alice Marcy, Scott P. Salowe and Douglas Wisniewski

It is certified that error appears in the above-identified patent and that said Letters Patent is hereby corrected as shown below:

On the face of the patent, following box [73], insert

- - [*] Notice: The term of this patent shall not extend beyond the expiration date of Patent No. 5,776,696. - -

Signed and Sealed this

Twentieth Day of October, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 1137 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:1:

| | | | | | |
|---|---|---|---|---|---|
| ATGGGAGTGC | AGGTGGAAAC | CATCTCCCCA | GGAGATGGAC | GCACCTTCCC | CAAGCGCGGC     60 |
| CAGACCTGCG | TGGTGCACTA | CACCGGGATG | CTTGAAGATG | GAAAGAAATT | TGATTCCTCC    120 |
| CGGGACAGAA | ACAAGCCCTT | TAAGTTTATG | CTAGGCAAGC | AGGAGGTGAT | CCGAGGCTGG    180 |
| GAAGAAGGGG | TTGCCCAGAT | GAGTGTGGGT | CAGAGAGCCA | AACTGACTAT | ATCTCCAGAT    240 |
| TATGCCTATG | GTGCCACTGG | GCACCCAGGC | ATCATCCCAC | CACATGCCAC | TCTCGTCTTC    300 |
| GATGTGGAGC | TTCTAAAACT | GGAAGGTCTG | GTTCCGCGTG | GATCCATGCC | AGATCCTGCA    360 |
| GCTCACCTGC | CCTTCTTCTA | CGGCAGCATC | TCGCGTGCCG | AGGCCGAGGA | GCACCTGAAG    420 |
| CTGGCGGGCA | TGGCGGACGG | GCTCTTCCTG | CTGCGCCAGT | GCCTGCGCTC | GCTGGGCGGC    480 |
| TATGTGCTGT | CGCTCGTGCA | CGATGTGCGC | TTCCACCACT | TTCCCATCGA | GCGCCAGCTC    540 |
| AACGGCACCT | ACGCCATTGC | CGGCGGCAAA | GCGCACTGTG | GACCGGCAGA | GCTCTGCGAG    600 |
| TTCTACTCGC | GCGACCCCGA | CGGGCTGCCC | TGCAACCTGC | GCAAGCCGTG | CAACCGGCCG    660 |
| TCGGGCCTCG | AGCCGCAGCC | GGGGGTCTTC | GACTGCCTGC | GAGACGCCAT | GGTGCGTGAC    720 |
| TACGTGCGCC | AGACGTGGAA | GCTGGAGGGC | GAGGCCCTGG | AGCAGGCCAT | CATCAGCCAG    780 |
| GCCCCGCAGG | TGGAGAAGCT | CATTGCTACG | ACGGCCCACG | AGCGGATGCC | CTGGTACCAC    840 |
| AGCAGCCTGA | CGCGTGAGGA | GGCCGAGCGT | AAACTTTACT | CTGGGGCGCA | GACCGACGGC    900 |
| AAGTTCCTGC | TGAGGCCGCG | GAAGGAGCAG | GGCACATACG | CCCTGTCCCT | CATCTATGGG    960 |
| AAGACGGTGT | ACCACTACCT | CATCAGCCAA | GACAAGGCGG | GCAAGTACTG | CATTCCCGAG   1020 |
| GGCACCAAGT | TTGACACGCT | CTGGCAGCTG | GTGGAGTATC | TGAAGCTGAA | GGCGGACGGG   1080 |
| CTCATCTACT | GCCTGAAGGA | GGCCTGCCCC | AACAGCAGTG | CCAGCAACGC | CTCTTAA      1137 |

( 2 ) INFORMATION FOR SEQ ID NO:2:

( i ) SEQUENCE CHARACTERISTICS:
    ( A ) LENGTH: 1155 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:2:

| | | | | | |
|---|---|---|---|---|---|
| ATGGGAGTGC | AGGTGGAAAC | CATCTCCCCA | GGAGATGGAC | GCACCTTCCC | CAAGCGCGGC     60 |
| CAGACCTGCG | TGGTGCACTA | CACCGGGATG | CTTGAAGATG | GAAAGAAATT | TGATTCCTCC    120 |
| CGGGACAGAA | ACAAGCCCTT | TAAGTTTATG | CTAGGCAAGC | AGGAGGTGAT | CCGAGGCTGG    180 |
| GAAGAAGGGG | TTGCCCAGAT | GAGTGTGGGT | CAGAGAGCCA | AACTGACTAT | ATCTCCAGAT    240 |
| TATGCCTATG | GTGCCACTGG | GCACCCAGGC | ATCATCCCAC | CACATGCCAC | TCTCGTCTTC    300 |

```
GATGTGGAGC TTCTAAAACT GGAAGGTCTG GTTCCGCGTG GATCCATGGC CAGCAGCGGC    360

ATGGCTGACA GCGCCAACCA CCTGCCCTTC TTTTTCGGCA ACATCACCCG GGAGGAGGCA    420

GAAGATTACC TGGTCCAGGG GGGCATGAGT GATGGGCTTT ATTTGCTGCG CCAGAGCCGC    480

AACTACCTGG GTGGCTTCGC CCTGTCCGTG GCCCACGGGA GGAAGGCACA CCACTACACC    540

ATCGAGCGGG AGCTGAATGG CACCTACGCC ATCGCCGGTG GCAGGACCCA TGCCAGCCCC    600

GCCGACCTCT GCCACTACCA CTCCCAGGAG TCTGATGGCC TGGTCTGCCT CCTCAAGAAG    660

CCCTTCAACC GGCCCCAAGG GGTGCAGCCC AAGACTGGGC CCTTTGAGGA TTTGAAGGAA    720

AACCTCATCA GGGAATATGT GAAGCAGACA TGGAACCTGC AGGGTCAGGC TCTGGAGCAG    780

GCCATCATCA GTCAGAAGCC TCAGCTGGAG AAGCTGATCG CTACCACAGC CCATGAAAAA    840

ATGCCTTGGT TCCATGGAAA AATCTCTCGG GAAGAATCTG AGCAAATTGT CCTGATAGGA    900

TCAAAGACAA ATGGAAAGTT CCTGATCCGA GCCAGAGACA ACAACGGCTC CTACGCCCTG    960

TGCCTGCTGC ACGAAGGGAA GGTGCTGCAC TATCGCATCG ACAAGACAA GACAGGGAAG   1020

CTCTCCATCC CCGAGGGAAA GAAGTTCGAC ACGCTCTGGC AGCTAGTCGA GCATTATTCT   1080

TATAAAGCAG ATGGTTTGTT AAGAGTTCTT ACTGTCCCAT GTCAAAAAAT CGGCACACAG   1140

GGAAATGTTA ATTAG                                                    1155

( 2 ) INFORMATION FOR SEQ ID NO:3:

( i ) SEQUENCE CHARACTERISTICS:
              ( A ) LENGTH: 675 base pairs
              ( B ) TYPE: nucleic acid
              ( C ) STRANDEDNESS: single
              ( D ) TOPOLOGY: linear ( i i ) MOLECULE TYPE: Genomic DNA ( x i ) SEQUENCE DESCRIPTION: SEQ ID NO:3:

ATGGGAGTGC AGGTGGAAAC CATCTCCCCA GGAGATGGAC GCACCTTCCC CAAGCGCGGC     60

CAGACCTGCG TGGTGCACTA CACCGGGATG CTTGAAGATG GAAAGAAATT TGATTCCTCC    120

CGGGACAGAA ACAAGCCCTT TAAGTTTATG CTAGGCAAGC AGGAGGTGAT CCGAGGCTGG    180

GAAGAAGGGG TTGCCCAGAT GAGTGTGGGT CAGAGAGCCA AACTGACTAT ATCTCCAGAT    240

TATGCCTATG GTGCCACTGG GCACCCAGGC ATCATCCCAC CACATGCCAC TCTCGTCTTC    300

GATGTGGAGC TTCTAAAACT GGAAGGTCTG GTTCCGCGTG GATCCATGGC GAACAGCCTG    360

GAGCCCGAAC CCTGGTTCTT CAAGAACCTG AGCCGCAAGG ACGCGGAGCG GCAGCTCCTG    420

GCGCCCGGGA ACACTCACGG CTCCTTCCTC ATCCGGGAGA GCGAGAGCAC CGCGGGATCG    480

TTTTCACTGT CGGTCCGGGA CTTCGACCAG AACCAGGGAG AGGTGGTGAA ACATTACAAG    540

ATCCGTAATC TGGACAACGG TGGCTTCTAC ATCTCCCCTC GAATCACTTT TCCCGGCCTG    600

CATGAACTGG TCCGCCATTA CACCAATGCT TCAGATGGGC TGTGCACACG GTTGAGCCGC    660

CCCTGCCAGA CCTAA                                                    675

( 2 ) INFORMATION FOR SEQ ID NO:4:

( i ) SEQUENCE CHARACTERISTICS:
              ( A ) LENGTH: 378 amino acids
              ( B ) TYPE: amino acid
              ( C ) STRANDEDNESS: single
              ( D ) TOPOLOGY: linear ( i i ) MOLECULE TYPE: protein ( x i ) SEQUENCE DESCRIPTION: SEQ ID NO:4:
```

-continued

| | | | | | | | | | | | | | | |
|---|---|---|---|---|---|---|---|---|---|---|---|---|---|---|
| Met 1 | Gly | Val | Gln | Val 5 | Glu | Thr | Ile | Ser | Pro 10 | Gly | Asp | Gly | Arg | Thr Phe 15 |
| Pro | Lys | Arg 20 | Gly | Gln | Thr | Cys | Val 25 | Val | His | Tyr | Thr | Gly 30 | Met | Leu Glu |
| Asp | Gly | Lys 35 | Lys | Phe | Asp | Ser 40 | Ser | Arg | Asp | Arg | Asn 45 | Lys | Pro | Phe Lys |
| Phe | Met 50 | Leu | Gly | Lys | Gln 55 | Glu | Val | Ile | Arg | Gly 60 | Trp | Glu | Glu | Gly Val |
| Ala 65 | Gln | Met | Ser | Val 70 | Gly | Gln | Arg | Ala | Lys 75 | Leu | Thr | Ile | Ser | Pro Asp 80 |
| Tyr | Ala | Tyr | Gly | Ala 85 | Thr | Gly | His | Pro | Gly 90 | Ile | Ile | Pro | Pro | His Ala 95 |
| Thr | Leu | Val | Phe 100 | Asp | Val | Glu | Leu | Leu 105 | Lys | Leu | Glu | Gly | Leu 110 | Val Pro |
| Arg | Gly | Ser 115 | Met | Pro | Asp | Pro | Ala 120 | Ala | His | Leu | Pro | Phe 125 | Phe | Tyr Gly |
| Ser | Ile | Ser 130 | Arg | Ala | Glu | Ala 135 | Glu | Glu | His | Leu | Lys 140 | Leu | Ala | Gly Met |
| Ala 145 | Asp | Gly | Leu | Phe | Leu 150 | Leu | Arg | Gln | Cys | Leu 155 | Arg | Ser | Leu | Gly Gly 160 |
| Tyr | Val | Leu | Ser | Leu 165 | Val | His | Asp | Val | Arg 170 | Phe | His | His | Phe | Pro Ile 175 |
| Glu | Arg | Gln | Leu | Asn 180 | Gly | Thr | Tyr | Ala | Ile 185 | Ala | Gly | Gly | Lys 190 | Ala His |
| Cys | Gly | Pro 195 | Ala | Glu | Leu | Cys | Glu 200 | Phe | Tyr | Ser | Arg | Asp 205 | Pro | Asp Gly |
| Leu | Pro 210 | Cys | Asn | Leu | Arg | Lys 215 | Pro | Cys | Asn | Arg | Pro 220 | Ser | Gly | Leu Glu |
| Pro 225 | Gln | Pro | Gly | Val | Phe 230 | Asp | Cys | Leu | Arg | Asp 235 | Ala | Met | Val | Arg Asp 240 |
| Tyr | Val | Arg | Gln | Thr 245 | Trp | Lys | Leu | Glu | Gly 250 | Glu | Ala | Leu | Glu | Gln Ala 255 |
| Ile | Ile | Ser | Gln 260 | Ala | Pro | Gln | Val | Glu 265 | Lys | Leu | Ile | Ala | Thr 270 | Thr Ala |
| His | Glu | Arg 275 | Met | Pro | Trp | Tyr | His 280 | Ser | Ser | Leu | Thr | Arg 285 | Glu | Glu Ala |
| Glu | Arg 290 | Lys | Leu | Tyr | Ser | Gly 295 | Ala | Gln | Thr | Asp | Gly 300 | Lys | Phe | Leu Leu |
| Arg 305 | Pro | Arg | Lys | Glu | Gln 310 | Gly | Thr | Tyr | Ala | Leu 315 | Ser | Leu | Ile | Tyr Gly 320 |
| Lys | Thr | Val | Tyr | His 325 | Tyr | Leu | Ile | Ser | Gln 330 | Asp | Lys | Ala | Gly 335 | Lys Tyr |
| Cys | Ile | Pro | Glu 340 | Gly | Thr | Lys | Phe | Asp 345 | Thr | Leu | Trp | Gln 350 | Leu | Val Glu |
| Tyr | Leu | Lys 355 | Leu | Lys | Ala | Asp | Gly 360 | Leu | Ile | Tyr | Cys | Leu 365 | Lys | Glu Ala |
| Cys | Pro 370 | Asn | Ser | Ser | Ala | Ser 375 | Asn | Ala | Ser | | | | | |

( 2 ) INFORMATION FOR SEQ ID NO:5:

( i ) SEQUENCE CHARACTERISTICS:
        ( A ) LENGTH: 384 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:5:

| Met | Gly | Val | Gln | Val | Glu | Thr | Ile | Ser | Pro | Gly | Asp | Gly | Arg | Thr | Phe |
| 1 | | | | 5 | | | | | 10 | | | | | 15 | |
| Pro | Lys | Arg | Gly | Gln | Thr | Cys | Val | Val | His | Tyr | Thr | Gly | Met | Leu | Glu |
| | | | 20 | | | | | 25 | | | | | 30 | | |
| Asp | Gly | Lys | Lys | Phe | Asp | Ser | Ser | Arg | Asp | Arg | Asn | Lys | Pro | Phe | Lys |
| | | 35 | | | | | 40 | | | | | 45 | | | |
| Phe | Met | Leu | Gly | Lys | Gln | Glu | Val | Ile | Arg | Gly | Trp | Glu | Glu | Gly | Val |
| | 50 | | | | 55 | | | | | 60 | | | | | |
| Ala | Gln | Met | Ser | Val | Gly | Gln | Arg | Ala | Lys | Leu | Thr | Ile | Ser | Pro | Asp |
| 65 | | | | 70 | | | | | 75 | | | | | | 80 |
| Tyr | Ala | Tyr | Gly | Ala | Thr | Gly | His | Pro | Gly | Ile | Ile | Pro | Pro | His | Ala |
| | | | 85 | | | | | 90 | | | | | 95 | | |
| Thr | Leu | Val | Phe | Asp | Val | Glu | Leu | Leu | Lys | Leu | Glu | Gly | Leu | Val | Pro |
| | | | 100 | | | | | 105 | | | | | 110 | | |
| Arg | Gly | Ser | Met | Ala | Ser | Ser | Gly | Met | Ala | Asp | Ser | Ala | Asn | His | Leu |
| | | 115 | | | | | 120 | | | | | 125 | | | |
| Pro | Phe | Phe | Phe | Gly | Asn | Ile | Thr | Arg | Glu | Glu | Ala | Glu | Asp | Tyr | Leu |
| | 130 | | | | | 135 | | | | | 140 | | | | |
| Val | Gln | Gly | Gly | Met | Ser | Asp | Gly | Leu | Tyr | Leu | Leu | Arg | Gln | Ser | Arg |
| 145 | | | | | 150 | | | | | 155 | | | | | 160 |
| Asn | Tyr | Leu | Gly | Gly | Phe | Ala | Leu | Ser | Val | Ala | His | Gly | Arg | Lys | Ala |
| | | | | 165 | | | | | 170 | | | | | 175 | |
| His | His | Tyr | Thr | Ile | Glu | Arg | Glu | Leu | Asn | Gly | Thr | Tyr | Ala | Ile | Ala |
| | | | 180 | | | | | 185 | | | | | 190 | | |
| Gly | Gly | Arg | Thr | His | Ala | Ser | Pro | Ala | Asp | Leu | Cys | His | Tyr | His | Ser |
| | | 195 | | | | | 200 | | | | | 205 | | | |
| Gln | Glu | Ser | Asp | Gly | Leu | Val | Cys | Leu | Leu | Lys | Lys | Pro | Phe | Asn | Arg |
| | 210 | | | | | 215 | | | | | 220 | | | | |
| Pro | Gln | Gly | Val | Gln | Pro | Lys | Thr | Gly | Pro | Phe | Glu | Asp | Leu | Lys | Glu |
| 225 | | | | | 230 | | | | | 235 | | | | | 240 |
| Asn | Leu | Ile | Arg | Glu | Tyr | Val | Lys | Gln | Thr | Trp | Asn | Leu | Gln | Gly | Gln |
| | | | | 245 | | | | | 250 | | | | | 255 | |
| Ala | Leu | Glu | Gln | Ala | Ile | Ile | Ser | Gln | Lys | Pro | Gln | Leu | Glu | Lys | Leu |
| | | | 260 | | | | | 265 | | | | | 270 | | |
| Ile | Ala | Thr | Thr | Ala | His | Glu | Lys | Met | Pro | Trp | Phe | His | Gly | Lys | Ile |
| | | 275 | | | | | 280 | | | | | 285 | | | |
| Ser | Arg | Glu | Glu | Ser | Glu | Gln | Ile | Val | Leu | Ile | Gly | Ser | Lys | Thr | Asn |
| | 290 | | | | | 295 | | | | | 300 | | | | |
| Gly | Lys | Phe | Leu | Ile | Arg | Ala | Arg | Asp | Asn | Asn | Gly | Ser | Tyr | Ala | Leu |
| 305 | | | | | 310 | | | | | 315 | | | | | 320 |
| Cys | Leu | Leu | His | Glu | Gly | Lys | Val | Leu | His | Tyr | Arg | Ile | Asp | Lys | Asp |
| | | | | 325 | | | | | 330 | | | | | 335 | |
| Lys | Thr | Gly | Lys | Leu | Ser | Ile | Pro | Glu | Gly | Lys | Lys | Phe | Asp | Thr | Leu |
| | | | 340 | | | | | 345 | | | | | 350 | | |
| Trp | Gln | Leu | Val | Glu | His | Tyr | Ser | Tyr | Lys | Ala | Asp | Gly | Leu | Leu | Arg |
| | | 355 | | | | | 360 | | | | | 365 | | | |
| Val | Leu | Thr | Val | Pro | Cys | Gln | Lys | Ile | Gly | Thr | Gln | Gly | Asn | Val | Asn |
| | 370 | | | | | 375 | | | | | 380 | | | | |

( 2 ) INFORMATION FOR SEQ ID NO:6:

( i ) SEQUENCE CHARACTERISTICS:
   ( A ) LENGTH: 224 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:6:

```
Met Gly Val Gln Val Glu Thr Ile Ser Pro Gly Asp Gly Arg Thr Phe
 1               5                  10                 15
Pro Lys Arg Gly Gln Thr Cys Val Val His Tyr Thr Gly Met Leu Glu
            20                  25                 30
Asp Gly Lys Lys Phe Asp Ser Ser Arg Asp Arg Asn Lys Pro Phe Lys
         35                  40                 45
Phe Met Leu Gly Lys Gln Glu Val Ile Arg Gly Trp Glu Glu Gly Val
     50                  55                 60
Ala Gln Met Ser Val Gly Gln Arg Ala Lys Leu Thr Ile Ser Pro Asp
 65                 70                 75                 80
Tyr Ala Tyr Gly Ala Thr Gly His Pro Gly Ile Ile Pro Pro His Ala
                 85                 90                 95
Thr Leu Val Phe Asp Val Glu Leu Leu Lys Leu Glu Gly Leu Val Pro
             100                 105                110
Arg Gly Ser Met Ala Asn Ser Leu Glu Pro Glu Pro Trp Phe Phe Lys
             115                 120                125
Asn Leu Ser Arg Lys Asp Ala Glu Arg Gln Leu Leu Ala Pro Gly Asn
     130                 135                 140
Thr His Gly Ser Phe Leu Ile Arg Glu Ser Glu Ser Thr Ala Gly Ser
145                 150                 155                160
Phe Ser Leu Ser Val Arg Asp Phe Asp Gln Asn Gln Gly Glu Val Val
                 165                 170                175
Lys His Tyr Lys Ile Arg Asn Leu Asp Asn Gly Gly Phe Tyr Ile Ser
             180                 185                 190
Pro Arg Ile Thr Phe Pro Gly Leu His Glu Leu Val Arg His Tyr Thr
         195                 200                 205
Asn Ala Ser Asp Gly Leu Cys Thr Arg Leu Ser Arg Pro Cys Gln Thr
 210                 215                 220
```

( 2 ) INFORMATION FOR SEQ ID NO:7:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:7:

```
Gly Leu Val Pro Arg Gly Ser
 1               5
```

( 2 ) INFORMATION FOR SEQ ID NO:8:

( i ) SEQUENCE CHARACTERISTICS:
   ( A ) LENGTH: 37 base pairs
   ( B ) TYPE: nucleic acid
   ( C ) STRANDEDNESS: single
   ( D ) TOPOLOGY: linear ( i i ) MOLECULE TYPE: Genomic DNA ( x i ) SEQUENCE DESCRIPTION: SEQ ID NO:8:

GATCGCCATG GGAGTGCAGG TGGAAACCAT CTCCCCA 37

( 2 ) INFORMATION FOR SEQ ID NO:9:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:9:

TACGAATTCT GGCGTGGATC CACGCGGAAC CAGACCTTCC AGTTTTAG 48

( 2 ) INFORMATION FOR SEQ ID NO:10:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:10:

ATTAGGATCC ATGCCAGATC CTGCAGCTCA CCTGCCCT 38

( 2 ) INFORMATION FOR SEQ ID NO:11:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:11:

ATATGGATCC TTACCAGAGG CGTTGCT 27

( 2 ) INFORMATION FOR SEQ ID NO:12:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:12:

CAATAGGATC CATGGCCAGC AGCGGCATGG CTGA 34

( 2 ) INFORMATION FOR SEQ ID NO:13:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:13:

GACCTAGGAT CCCTAATTAA CATTTCCCTG TGTGCCGAT 39

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

ATATGGATCC ATGGCGAACA GCCTGGAGCC CGAACCCT        38

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

ATTAGGATCC TTAGGTCTGG CAGGGGCGGC TCAACCGTGT GCA        43

(2) INFORMATION FOR SEQ ID NO:16:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 6...6
        (D) OTHER INFORMATION: Xaa =Phosphorylated Tyrosine
        (A) NAME/KEY: Other
        (B) LOCATION: 17...17
        (D) OTHER INFORMATION: Xaa =Phosphorylated Tyrosine (xi) SEQUENCE DESCRIPTION: SEQ ID NO:16:

Gly Ser Asn Gln Leu Xaa Asn Glu Leu Asn Leu Gly Arg Arg Glu Glu
1               5               10              15

Xaa Asp Val Leu Asp Lys
          20

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 4...4
        (D) OTHER INFORMATION: Xaa =Phosphorylated Tyrosine (xi) SEQUENCE DESCRIPTION: SEQ ID NO:17:

Glu Pro Gln Xaa Glu Glu Ile Pro Ile Tyr Leu
1               5               10